United States Patent [19]

Cohen et al.

[11] Patent Number: 4,945,911

[45] Date of Patent: Aug. 7, 1990

[54] MEDICAL ELECTRODE

[76] Inventors: Joel Cohen; Esther R. Cohen, both of 1020 NW. 99th Ave., Plantation, Fla. 33322

[21] Appl. No.: 146,755

[22] Filed: Jan. 22, 1988

[51] Int. Cl.⁵ .......................................... A61B 5/0402
[52] U.S. Cl. ..................................... 128/640; 128/641
[58] Field of Search ............................... 128/639–641, 128/644, 798, 802, 803

[56] References Cited

U.S. PATENT DOCUMENTS

| | | | |
|---|---|---|---|
| 3,834,373 | 9/1974 | Sato | 128/640 |
| 3,862,633 | 1/1975 | Allison et al. | 128/641 |
| 3,901,218 | 8/1975 | Buchalter | 128/641 |
| 4,270,543 | 6/1981 | Tabuchi et al. | 128/639 |
| 4,319,579 | 3/1982 | Cartmell | 128/803 X |
| 4,409,981 | 10/1983 | Lundberg | 128/640 |
| 4,490,005 | 12/1984 | Hovey | 128/641 |
| 4,635,642 | 1/1987 | Cartmell et al. | 128/639 |
| 4,653,501 | 3/1987 | Cartmell et al. | 128/640 |

*Primary Examiner*—Lee S. Cohen
*Attorney, Agent, or Firm*—Malloy & Malloy

[57] ABSTRACT

A medical electrode composed of a cylindrical portion open at one end and closed at the other end with only an opening for snug passage of a male projecting portion of a head connected to a lead wire and, at the other end, having a flange, the cylindrical portion being filled with a conductive adhesive gel which projects axially from the flange with a removable liner normally protecting the adhesive gel and to be removed for use.

4 Claims, 1 Drawing Sheet

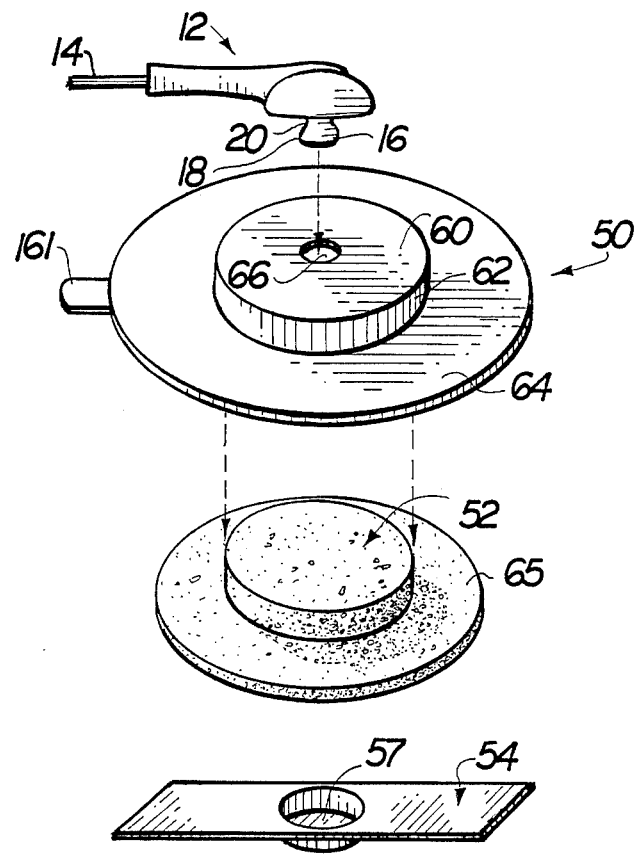
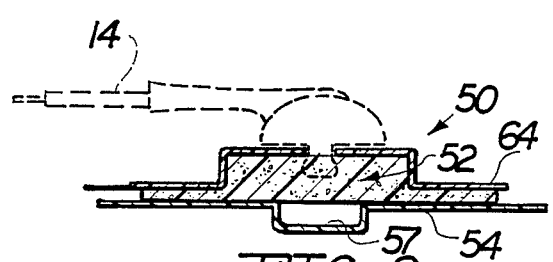
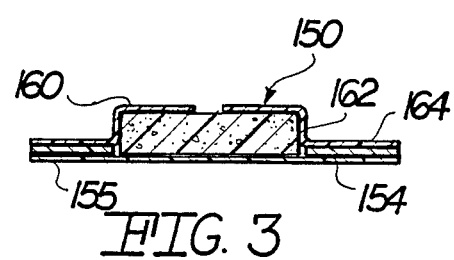
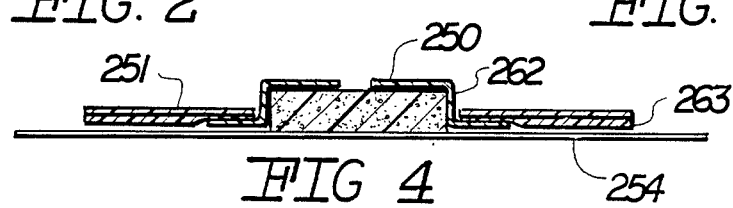
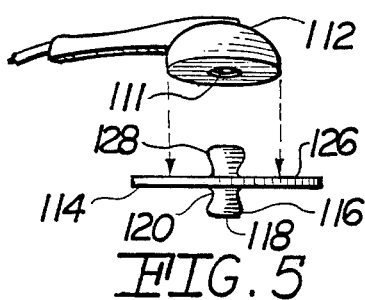

MEDICAL ELECTRODE

BACKGROUND OF THE INVENTION

Field of the Invention

There are numerous types of electrodes which are adapted to be secured to the human body for taking electrical measurements. This invention is of such an electrode and it is of improved construction. The structure of the electrode of the present invention includes a cylindrical portion a) open at one end which one end has an outwardly extending flange end, and b) at the other end, the cylindrical portion is substantially closed by an annular member which has a central opening. This central opening is sized for snug captivating passage of the male projecting portion of a conventional male head of a lead wire. The distal end of the male portion is captivated in conductive adhesive gel within the cylindrical portion. The adhesive gel is of an axial length greater than the projecting length of the head captivated in it and the gel extends slightly beyond the flange. The terminal end of the gel projecting beyond the flange is protectively covered by a removable liner, which may be removed. Thereafter, the gel is applied to the body of a wearer to which it is adhesively secured by the adhesive in the gel.

Summary of the Invention

Two embodiments are disclosed. In one, the adhesive and conductive gel mixture extends axially from the cylindrical portion and also coats the flange portion. In the other embodiment, the adhesive conductive gel extends axially and generally cocylindrically from the cylindrical portion. In either event, a liner is utilized; however, in the first of these two embodiments, the increased adhesive area which is exposed when the liner is removed gives the electrode a somewhat longer and stronger adhering quality with the skin of a wearer than does the second embodiment. One embodiment can be considered to be for a relatively longer-term use as in a stress test, while the other is for a short-term use, such as for use in a resting electrode cardiogram.

In another embodiment of the invention, there is an enlarged annular member which is provided on the flange. It is adhesively bonded to the flange and extends outwardly from the flange so that an enlarged area of adhesive contact with the wearer can be achieved.

There has been a problem in the prior art in that most heads currently utilize female heads. In order to utilize the instant invention, there is provided, in one embodiment of the invention, an adapter which includes a male portion to connect with the conventional female head and a male portion for cooperation with the electrode as described above.

DESCRIPTION OF THE DRAWINGS

FIG. 1 is an exploded perspective view of the invention in one embodiment,

FIG. 2 is a view in cross-section of the product in FIG. 1 as assembled;

FIG. 3 is a view in cross-section of the second embodiment;

FIG. 4 is a view in cross-section of the third embodiment, and

FIG. 5 illustrates the adapter in use.

BRIEF DESCRIPTION OF THE PREFERRED EMBODIMENT

Referring to the drawings, there is shown a conventional head 12 on a lead wire 14. As shown, the head is provided with a projecting portion 16 of predetermined size and configuration. It has distal end 18 which is enlarged defining a constricted neck portion 20 and a bulbous terminal end. This head is for mating with the electrode to be described more fully hereinafter. It will be seen that this head is companionate to the electrode of this invention. On the other hand, however, many of the heads, such as 112 are female as at 111, see FIG. 5. To adapt such female heads for use with the present invention, an adapter is provided which includes a plate portion 114 and a projecting portion 116 which has a bulbous distal end 118 and constricted neck 120 which matches the configuration of that of the head described above. This adapter is provided, on the opposite face 126, with a projecting portion 128 which is sized configured and adapted for electrical engagement in the recess 111 of the female head 112. In any event, the electrode, now to be described, is for use with either the male head configured for companionate use with it or, optionally, the female head provided with the adapter as described.

Turning now to the electrode itself, it is seen to be composed of a base portion 50, a wad of conductive adhesive gel 52 and a liner 54 which protectively overlays the adhesive gel.

Referring more in detail to the base, it is of non-conductive, plastic, bendable and resilient material. It is configured so that it has an annular plate portion 60 and an axially extending cylindrical portion 62 which, at its terminal open end has an out-turned flange portion 64. It is seen that there is a central opening 66 in the plate portion which is sized and shaped for companionate but snug passage of the bulbous end 18 of the head or, in the case of the use of the adapter, the head 118. The cylindrical portion extending away from the plate, is of a predetermined axial length and the conductive gel fills the cylindrical portion and also includes a portion 65 which may, in the embodiment shown in FIG. 2, coat the flange. In the preferred embodiment, the liner 54 may be provided with a well 57 so that, when the bulbous portion of the head is inserted through the opening 66, there will be some give on the lower end of the gel.

The embodiment shown in FIG. 3 is a slightly modified version of the electrode. Once again the base 150 is seen to include the plate portion 160, the cylindrical portion 162 and the flange portion 164. In this embodiment, however, the adhesive conductive gel extends axially from the base portion but does not coat the flange. An annular adhesive means 154 is provided on the flange with a liner 155 which is adapted to be removed to expose the adhesive gel.

Referring to the embodiment shown in FIG. 4, the base 250 is seen to include the same structure as that described above in connection with FIG. 3 with the additional feature that an annular member 251 is adhesively secured to the surface of the flange nearest to the plate portion. This annular member includes a outwardly extending portion around the cylindrical portion 262 which has adhesive means such as 263 which, when the liner 254 is removed, exposes the adhesive so that there is a relatively large area for adhesive contact.

In use of the several embodiments, the liner 54, or 155 or 254 is peeled away, exposing the adhesive conductive gel. The electrode is then applied with pressure to a selected zone of the skin of a user. Either before or after that is done, the bulbous end of the protecting portion of the head is forceably inserted through the opening, see FIG. 2 and the dotted line position there shown. Thereafter, electrical current through the lead wire 14 is conducted through the adhesive conductive gel 52 so that readings for the purpose of recording patient information or, as is sometimes used, for electrical stimulation of the skin. With respect to the embodiment shown in FIG. 4, it will be seen that, since the gel is completely protectively covered by the liner, it does not necessarily have to be a conductive gel which is adhesive but, alternatively, may be what is known in the field as hard conductive gel or a wet conductive gel impregnated sponge.

It is thus seen that there has been provided an electrode which provides for fast connection and disconnection of headed lead wires from electro-cardiogram equipment for example. The lift tab 161 preferably provided on the base provides for ease of removal after use.

What is claimed is:

1. An electrode to connect to the head of a lead wire which head has a male projecting portion of predetermined size and configuration having an enlarged distal end, said male projecting portion being of a first overall predetermined length, said electrode including:
   (A) a base of non-conductive, plastic, bendable and resilient material and comprising:
      (a) an annular plate portion with a central opening of predetermined companionate shape for tight passage of said enlarged distel end of said projecting portion and said opening being foreshortenly sized with respect to the cross-sectional area of said projecting portion to permit forced passage of the enlarged distal end through said opening,
      (b) a cylindrical portion extending away from said plate portion a first predetermined distance to a terminal end, and
      (c) an out-turned flange on the terminal end of the cylindrical portion spaced from the plane of said plate portion and in generally parallel relation thereto, and said flange having a distal surface about the cylindrical portion facing toward the plate portion and an annular proximal surface to abut the skin of a wearer,
   (B) conductive gel defining a cylindrical plug filling the cylindrical portion and extending axially from the proximal surface a distance slightly greater than the distance from said plate portion to said flange proximal surface, said plug having a terminal end generally parallel to said proximal surface and said plug including a portion coating said annular proximal surface,
   a linear means removably and normally protectively overlaying said terminal end of said plug, said terminal end of said plug including an adhesive means to removably apply the electrode to the skin of a person; said adhesive means and gel comprising a mixture, and
   (C) the axial distance from the plate portion through the axial length of the gel being greater than said first predetermined length.

2. The electrode as set forth in claim 1 wherein said flange includes a tab.

3. The electrode as set forth in claim 1, wherein said liner means is generally planar.

4. The electrode as set forth in claim 1, wherein said liner means includes a centrally located well portion generally coaxial with said cylindrical portion.

* * * * *